United States Patent
Lee

(10) Patent No.: US 8,116,991 B2
(45) Date of Patent: Feb. 14, 2012

(54) DEVICE FOR MEASURING THE FLOW RATE OF RINGER SOLUTION

(76) Inventor: Doo Yong Lee, Daejeon (KR)

( * ) Notice: Subject to any disclaimer, the term of this patent is extended or adjusted under 35 U.S.C. 154(b) by 242 days.

(21) Appl. No.: 12/517,064

(22) PCT Filed: Dec. 10, 2007

(86) PCT No.: PCT/KR2007/006394
§ 371 (c)(1),
(2), (4) Date: May 30, 2009

(87) PCT Pub. No.: WO2008/082091
PCT Pub. Date: Jul. 10, 2008

(65) Prior Publication Data
US 2010/0063752 A1     Mar. 11, 2010

(30) Foreign Application Priority Data
Dec. 29, 2006  (KR) .................... 10-2006-0137420

(51) Int. Cl.
*G01F 1/00*  (2006.01)
(52) U.S. Cl. ................. 702/46; 702/45; 702/50; 73/861
(58) Field of Classification Search .................... 702/65, 702/46, 45, 50; 604/253; 73/861
See application file for complete search history.

(56) References Cited

U.S. PATENT DOCUMENTS
4,094,318 A * 6/1978 Burke et al. .................... 604/65
4,820,281 A * 4/1989 Lawler, Jr. .................... 604/253

OTHER PUBLICATIONS
International Search Report for application PCT/KR2007/006394 filed on Dec. 10, 2007.

\* cited by examiner

*Primary Examiner* — Eliseo Ramos Feliciano
*Assistant Examiner* — Manuel Rivera Vargas

(57) ABSTRACT

A device for measuring a flow rate of Ringer's solution includes a key input unit including a number input key through which a user can make an input each time when a drip drips in a drip chamber; a power supply unit for supplying power; an oscillation circuit for oscillating a signal having a preset frequency; a display unit for quantitatively outputting a calculated flow rate of Ringer's solution; and a control unit for calculating an elapsed time when the input is made through the number input key of the key input unit for a preset number of times, calculating the number of drips per an hour using the preset number of times and the calculated elapsed time, acquiring a quantitative flow rate of Ringer's solution by multiplying a preset volume of each drip and the calculated number of drips, and outputting the acquired flow rate to the display unit.

3 Claims, 2 Drawing Sheets

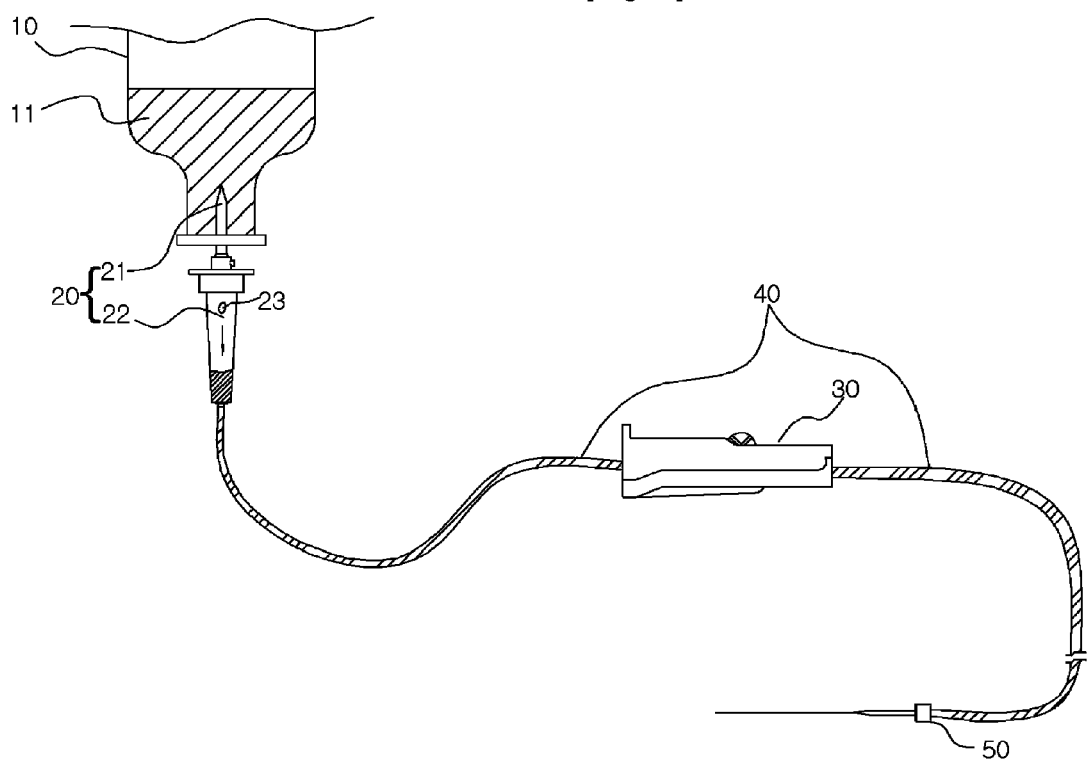
[Fig. 1]
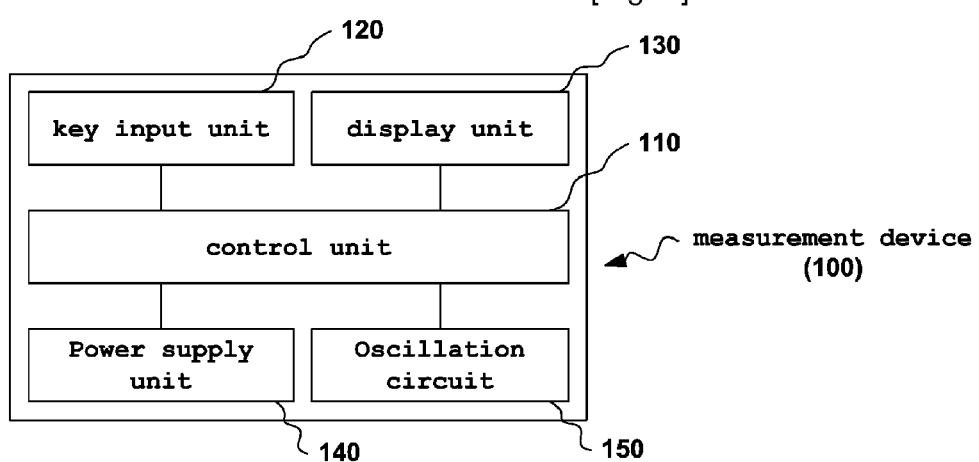
[Fig. 2]

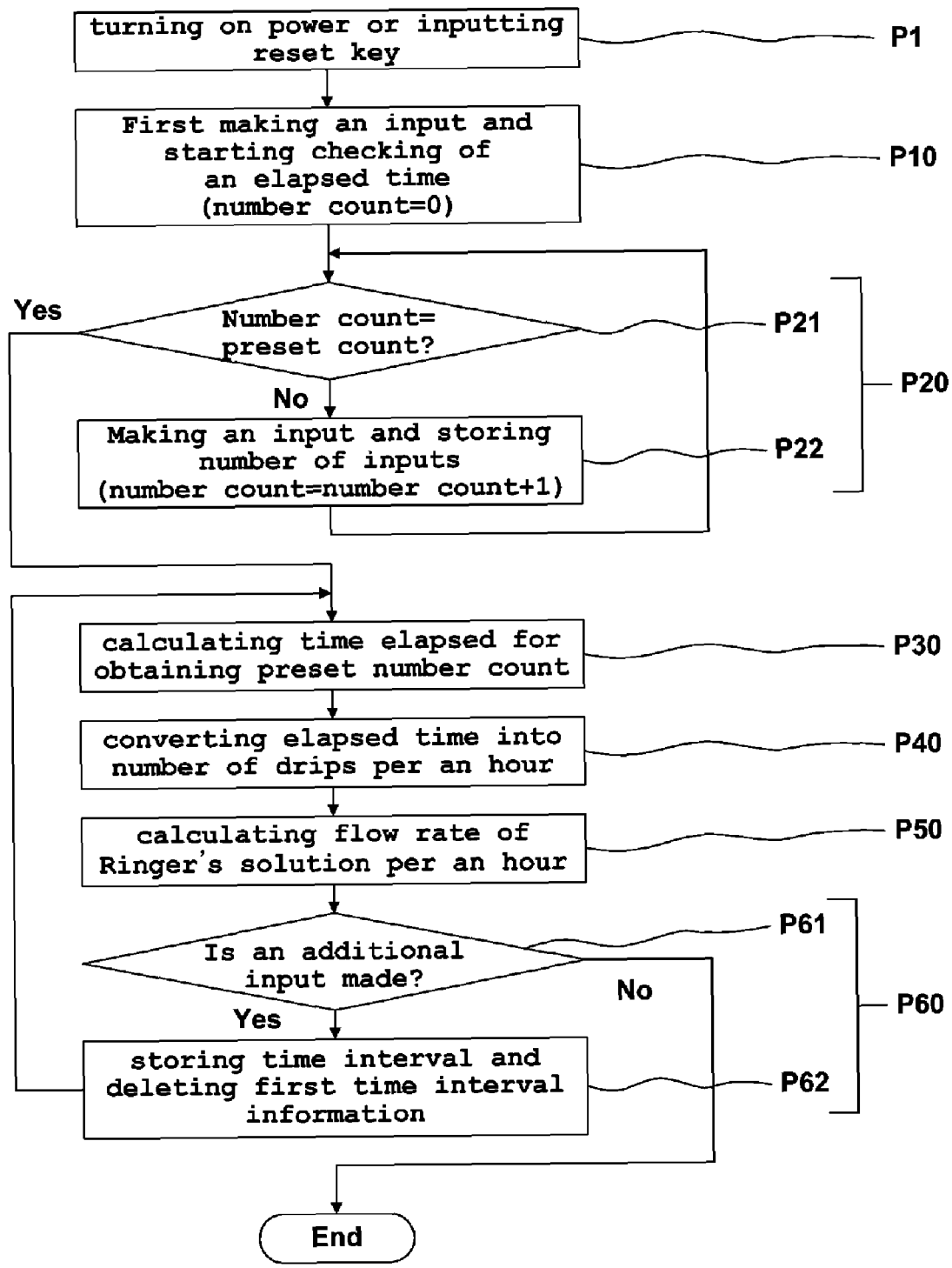

DEVICE FOR MEASURING THE FLOW RATE OF RINGER SOLUTION

TECHNICAL FIELD

The present invention relates to a device for measuring the flow rate of Ringer's solution, and more particularly to a portable device for measuring the flow rate of Ringer's solution, which can measure, as a quantitative rate, the amount of Ringer's solution flowing through an intravenous injection needle.

BACKGROUND ART

Referring to FIG. 1, as is generally known in the art, an intravenous injection system for directly injecting medicine into a vein includes a bottle 10 containing Ringer's solution 11, a dripper 20 composed of an insertion needle 21 which is inserted through a closure lid provided to the bottle 10 and allows the Ringer's solution 11 to flow therethrough and a drip chamber 22 which is formed to allow the Ringer's solution 11 to drop in the shape of a drip 23 therein, an injection needle 50 to be inserted into the vein, a tube 40 connecting the dripper 20 and the injection needle 50 with each other and allowing the Ringer's solution 11 to flow therethrough, and an adjustment clamp 30 fitted around the intermediate portion of the injection tube 40 to allow the flow rate of the Ringer's solution 11 to be adjusted.

In an intravenous injection method using the intravenous injection system constructed as mentioned above, by fixedly placing the bottle 10 higher than the injection needle 50, the Ringer's solution 11 can be naturally injected into the vein due to the gravity of the Ringer's solution. In a procedure for adjusting the flow rate of the Ringer's solution 11, the drop cycle of the drip 23 can be changed as a user manipulates the adjustment clamp 30. In the adjustment procedure, a predetermined number of drips 23 are counted with the naked eye, and an elapsed time is checked by using a watch. Usually, as a doctor writes on a chart the number of drips 23 per minute and transfers the chart to a nurse, the nurse can adjust the dropping speed of the drip 23 by manipulating the adjustment clamp 30.

However, in this procedure for adjusting the flow rate of the Ringer's solution, since the procedure is implemented depending upon the user's eyes based on experience, it is difficult to precisely adjust the flow rate of Ringer's solution. In general, Ringer's solution must be injected by determining a flow rate in consideration of a patient's age, body and condition, the kind and the volume of Ringer's solution, and so forth. In this regard, because the adjustment procedure cannot precisely adjust the flow rate of Ringer's solution, a medical accident is likely to occur.

Therefore, it is necessary to quantitatively measure the flow rate of Ringer's solution so that the adjustment clamp 30 can be appropriately manipulated. In this regard, prior arts are disclosed in Korean Unexamined Patent Publication No. 2004-0048889 entitled "Volumetric flow measurement device for intravenous injection set" and Korean Unexamined Patent Publication No. 2005-0039780 entitled "A system for measuring the flow rate of Ringer's solution using a method of image signal processing." Nevertheless, in these prior arts, since a drip in a drip chamber is sensed using infrared rays and the number of drips and the quantitative amount of Ringer's solution are determined, a precision can be deteriorated due to the influence by outside light, and when installing the device or system for measuring the flow rate of Ringer's solution, inconvenience is caused and a substantial cost is required. Due to these facts, the device or system could not be actually employed on a commercial scale.

Also, there has been disclosed Korean Utility Model Registration No. 20-0336940 entitled "Automatic detecting and pre-warning system for medicine instiller." This system has a drop carrier which moves each time a drip drips in a drip chamber so that the flow rate of Ringer's solution can be measured from the outside. Nonetheless, this system suffers from defects in that the structure of a drip chamber should be changed and the system cannot be practically used due to the complexity of the drip chamber and the system.

Further, because the prior arts basically adopt a process of measuring a volume by a sensor, they cannot help but adjust the flow rate of Ringer's solution by entirely relying on the operation of the measurement device or system. In this connection, since it is difficult to properly handle a situation where the measurement device or system misoperates, demand exists for a measurement device which can be conveniently used by a doctor in charge or a person in charge of nursing and is free from troubles.

That is to say, because the measurement device or systems according to the prior arts cannot be practically used due to the problems described above, it is the norm in a hospital or a doctor's office for a nurse to measure the time during which a predetermined number of drips drip, using a watch having a second hand, and to calculate the flow rate of Ringer's solution. In this procedure, since it is necessary to alternately look at the watch and a drip chamber, an error is likely to be caused in the calculated flow rate. Hence, demands exist for a device for measuring the flow rate of Ringer's solution, which can be conveniently used, even by an unskilled person in charge of nursing.

DISCLOSURE OF INVENTION

Technical Problem

Therefore, the present invention has been made in view of the above-mentioned problems, and an object of the present invention is to provide a device for measuring the flow rate of Ringer's solution which can be conveniently carried and precisely measure the flow rate of Ringer's solution while obviating the need for installing a complicated measurement structure in a drip chamber.

Another object of the present invention is to provide a device for measuring the flow rate of Ringer's solution which can display the flow rate of Ringer's solution by a quantitative rate having a generally used unit (ml/hr) so that a nurse can easily manipulate an adjustment clamp in correspondence with a desired flow rate of Ringer's solution.

Still another object of the present invention is to provide a device for measuring the flow rate of Ringer's solution which can measure the flow rate of Ringer's solution without using a costly measurement apparatus, and therefore can be widely distributed over hospitals and doctors' offices.

A still further object of the present invention is to provide a device for measuring the flow rate of Ringer's solution which allows even an unskilled person in charge of nursing to easily and precisely check the flow rate of Ringer's solution.

Technical Solution

In order to achieve the above objects, according to one aspect of the present invention, there is provided a device for measuring a flow rate of Ringer's solution, comprising a key input unit 120 including a number input key through which a user can make an input each time a drip 23 drips in a drip chamber 22; a power supply unit 140 for supplying power; an oscillation circuit 150 for oscillating a signal having a preset frequency; a display unit 130 for quantitatively outputting a calculated flow rate of Ringer's solution; and a control unit 110 for calculating an elapsed time when the input is made through the number input key of the key input unit 120 for a preset number of times, calculating the number of drips per an hour using the preset number of times and the calculated elapsed time, acquiring a quantitative flow rate of Ringer's solution by multiplying a preset volume of each drip 23 and the calculated number of drips per an hour, and outputting the acquired flow rate to the display unit 130.

According to another aspect of the present invention, when the input through the number input key is made more than a preset number of times, the control unit 110 calculates an elapsed time for the preset number of times before a final input time, calculates the number of drips per an hour using the preset number of times and the calculated elapsed time, acquires a quantitative flow rate of Ringer's solution by multiplying a preset volume of each drip 23 and the calculated number of drips per an hour, and outputs the acquired flow rate to the display unit 130.

According to still another aspect of the present invention, the key input unit 120 further includes a selection key for selecting a volume of each drip 23 depending upon a use of Ringer's solution, and the control unit 110 stores information for volumes of a plurality of drips, which are preset to be different from one another depending upon a use of Ringer's solution and calculates a flow rate of Ringer's solution using a selected volume of each drip 23, which is selected through the selection key.

According to a still further aspect of the present invention, there is provided a method for measuring a flow rate of Ringer's solution using a device for measuring a flow rate of Ringer's solution, in which a user makes an input each time when a drip 23 drops in a drip chamber 22, an elapsed time is calculated when the input is made for a preset number of times, and a quantitative flow rate is acquired according to a preset volume of each drip 23, the method comprising the steps of starting to check a time interval from when a first input is made (P10); continuously receiving inputs for a preset number of times after the first input is made in step P10 and storing time intervals every time when the inputs are made (P20); calculating a time elapsed for receiving the inputs for the preset number of times (P30); converting the preset number of times for the elapsed time calculated in step P30 into the number of drips per an hour (P40); calculating a flow rate of Ringer's solution per an hour by multiplying a preset volume of each drip and the number of drips per an hour converted in step P40, and outputting the calculated flow rate of Ringer's solution (P50); and storing a time interval when an input is additionally made within a predetermined time after step P50, and returning to step P30 by deleting the first time interval that is used when calculating the elapsed time in step P30 and allowing the stored time interval to be used in calculation of an elapsed time (P60).

Advantageous Effects

Thanks to the features of the present invention, the device can be manufactured to have a small volume so that the device can be conveniently manipulated with one hand, and the accurate flow rate of Ringer's solution can be outputted as a quantitative value so that a user can easily adjust the flow rate of Ringer's solution with the other hand.

Also, in the present invention, since the user can directly measure and check the flow rate of Ringer's solution, the reliability of the device can be improved, and since the flow rate of Ringer's solution can be measured in a short time, convenience can be provided to the user, and even an unskilled person in charge of nursing can precisely measure the flow rate of Ringer's solution.

Further, in the present invention, when compared to conventional measurement devices or systems, because the device is applied to the field of injecting Ringer's solution, the device can be widely distributed over hospitals and doctor's offices.

BRIEF DESCRIPTION OF THE DRAWINGS

The foregoing and other objects, features and advantages of the present invention will become more apparent from the following detailed description when taken in conjunction with the accompanying drawings in which:

FIG. 1 is a view illustrating the construction of a conventional intravenous injection system;

FIG. 2 is a view illustrating the construction of a device for measuring the flow rate of Ringer's solution in accordance with an embodiment of the present invention; and FIG. 3 is a flow chart illustrating a method for measuring the flow rate of Ringer's solution in accordance with another embodiment of the present invention.

10: bottle 11: ringer's solution 20: dripper
21: insertion needle 22: drip chamber 23: drip
30: adjustment clamp 40: injection tube 50: injection needle
100: measurement device
110: control unit 120: key input unit 130: display unit
140: power supply unit 150: oscillation circuit

BEST MODE FOR CARRYING OUT THE INVENTION

FIG. 2 is a view illustrating the construction of a device 100 for measuring the flow rate of Ringer's solution in accordance with an embodiment of the present invention.

Referring to FIG. 2, the device 100 for measuring the flow rate of Ringer's solution according to the present invention includes a key input unit 120 for permitting a key input from a user, a power supply unit 140 for supplying power to the respective component parts of the device 100 for measuring the flow rate of Ringer's solution, an oscillation circuit 150 for oscillating a signal having a preset frequency, a display unit 130 for outputting the calculated flow rate of Ringer's solution as a quantitative value, and a control unit 110 for controlling the operations of these sections and circuits 120, 130, 140 and 150.

In detail, the key input unit 120 has a number input key which is provided to allow the user to input a number signal each time when the drip 23 drops in the drip chamber 22, a reset key which is provided to allow the user to initiate the operation of the device 100 so as to measure the flow rate of Ringer's solution, and a power key which is provided to allow the user to permit or interrupt the power supply from the power supply unit 140 to the respective component parts of the device 100 for measuring the flow rate of Ringer's solution.

The control unit 110 is initiated when the user turns on the device 100 for measuring the flow rate of Ringer's solution via the power key or presses the reset key, so that the flow rate of Ringer's solution can be measured. When the control unit 110 is in the initiated state, if the user starts to press the number input key, the flow rate of the Ringer's solution can be calculated.

That is to say, the control unit 110 calculates an elapsed time using the signal from the oscillation circuit 150 when a number input has been made a preset number of times via the number input key of the key input unit 120. Then, the control unit 110 converts the preset number of times for the elapsed time into the number of drips 23 per an hour, acquires the quantitative flow rate of the Ringer's solution by multiplying the predetermined volume of the drip 23 and the converted number of drips 23 per an hour, and outputs the acquired flow rate to the display unit 130.

Additionally describing the predetermined volume of the drip 23, in general, the Ringer set including the respective component parts 20, 30, 40 and 50 are integrally manufactured. The insertion needle 21 and the drip chamber 22 are formed such that the volume of the drip 23, which drips in the drip chamber 22 after flowing through the insertion needle 21, is constant. For example, a Ringer set for injecting common Ringer's solution is formed to have 15 drips 23 per 1 ml, and a Ringer set for a newborn baby is formed to have 60 drips per 1 ml. Also, a Ringer set for injecting special Ringer's solution such as nutrition solution is formed to have the same volume as the drip 23 of the common Ringer's solution when the Ringer set is provided as an integral set with a bottle. The reason why the Ringer sets are formed in these ways resides in that the dripping drip 23 can be viewed with naked eyes, and an elapsed time can be checked using a watch so that the flow rate of the Ringer's solution can be known.

Accordingly, the volume of the drip 23 that is stored in the control unit 110 can be preset to 1/15 ml or 1/60 ml. Also, it can be envisaged that the volumes of drips 23 for both an adult and a new-born baby are stored in the control unit 110 and an input key for selecting any one volume is included in the key input unit 120 so that the control unit 110 can implement selective calculation. Preferably, by outputting an advisory note or a guide lamp for a common use or a use for a new-born baby, it is possible to avoid a medial accident.

FIG. 3 is a flow chart illustrating a method for measuring the flow rate of Ringer's solution using the device constructed as shown in FIG. 2.

In the following description, the method for measuring the flow rate of Ringer's solution will be explained assuming that the preset number of times of dripping of the drip 23 is 4. It is to be noted that the time measured between a first input from the number input key and a fifth input from the number input key represents the time that is elapsed while the drip 23 drips four times.

First, as the user turns on the power key of the key input unit 120, the power from the power supply unit 140 is supplied to the respective component parts of the measurement device 100. At this time, the device 100 for measuring the flow rate of Ringer's solution is initiated to calculate the flow rate of Ringer's solution. Further, when the user presses the reset key, the device 100 for measuring the flow rate of Ringer's solution can initiate the procedure for measuring the flow rate of Ringer's solution, which will be described below (P1).

In the device 100 for measuring the flow rate of Ringer's solution initiated in this way, as the first drip 23 drips and the user presses the number input key from which the input time interval of the number input key begins to be checked, the number of inputs from the number input key (that is, a number count) is set to 0 (P10).

Then, in the flow rate measurement device 100, the number count is compared with the preset number (i.e. 4) of times (P21), the number input key is inputted one time each time when the drip 23 drips in the drip chamber 22 (P22), and when the total number of input times through the number input key corresponds to 4, the method proceeds to the step of calculating the flow rate of Ringer's solution (P20). In the meanwhile, the device 100 for measuring the flow rate of Ringer's solution stores the input time intervals of the respective inputs from the number input key.

The device 100 for measuring the flow rate of Ringer's solution calculates the time elapsed while the number input key is pressed four times (P30), and converts the number of drips 23, that is, 4, per the calculated elapsed time into the number of drips 23 per an hour (P40). Next, the device 100 calculates a quantitative flow rate (ml/hr) using the predetermined volume of the drip 23 and the converted number of drips 23 per an hour and outputs the calculated quantitative flow rate to the display unit 130 (P50).

Furthermore, the device 100 for measuring the flow rate of Ringer's solution checks if there is an additional input through the number input key after step P50 to continuously measure the flow rate of Ringer's solution (P61). If there is the additional input through the number input key, an input time interval is stored (P62) and step P30 is implemented and the flow rate of Ringer's solution is recalculated through steps P40 and P50. When the method proceeds to step P30, the first input time interval that is used when calculating the elapsed time in step P30 is deleted (P60), and an elapsed time is calculated in step P30 for the four inputs through the number input key, including the input through the number input key in step P60.

In step P30, in the course of counting the number of times through which the drips 23 drop, since the elapsed time is measured from the first drop time in step P10 to the fifth drop time, the calculation is implemented by excluding the time elapsed until the first drip 23 drops. Accordingly, it is possible to solve the problem caused due to the fact that the time interval elapsed from the time when a drip 23 before the first drip 23 drops to the time when the first drip 23 drops varies depending upon a patient. In addition, when the user thinks that the flow rate obtained through the five drips 23 is inaccurate and continuously presses the number input key every time when the drips 23 drop as in step P60, the device 100 for measuring the flow rate of Ringer's solution recalculates and outputs the flow rate for the latest four drips 23 every time when the input from the number input key is made. For example, if the number input key is inputted for a total of seven drips, when the fifth input is made, the flow rate for second, third, fourth and fifth drips 23 is calculated and outputted to the display unit 130. Further, when the sixth input is made, the flow rate for third, fourth, fifth and sixth drips 23 is calculated and outputted to the display unit 130. Moreover, when the seventh input is made, the flow rate for fourth, fifth, sixth and seventh drips 23 is calculated and outputted to the display unit 130.

While the explanations have been given assuming that the flow rate is calculated for a total of four effective drips 23, the number of drips 23 can be changed in order to improve the precision of the measurement device 100 or in consideration of the time elapsed in the measurement procedure.

Besides, while it was described in the embodiment shown in FIG. 3 that the time intervals elapsed while the drips 23 drop are stored and the elapsed time for the preset number of times (that is, four times) is calculated, it can be contemplated that the calculation of the elapsed time can be implemented in such a way as to store not the time intervals while the drips 23 drip, but the times when the drips 23 drop. In other words, the control unit 110 can calculate the elapsed time for the four drips 23 by subtracting the input time of the first input from the input time of the fifth input.

In addition, the device 100 for measuring the flow rate of Ringer's solution can restart the measurement procedure from step P10 when the reset key is inputted.

The invention claimed is:

1. A portable device for measuring a flow rate of Ringer's solution, comprising:
   a key input unit including a number input key through which a user can provide an input each time a drip drips in a drip chamber;
   a power supply unit for supplying power;
   an oscillation circuit for oscillating a signal having a preset frequency;
   a display unit for quantitatively outputting a calculated flow rate of Ringer's solution; and
   a control unit configured to:
      (a) determine whether the number of inputs provided for by the user exceeds a preset drip number,
      (b) when the number of inputs provided by the user does not exceed the preset drip number, the control unit is further configured to:
         obtain an elapsed time when the number of inputs provided by the user reaches the preset drip number,
         calculate the number of drips per hour using the preset drip number and the elapsed time,
         calculate a quantitative flow rate of Ringer's solution by multiplying a preset volume of each drip and the calculated number of drips per hour, and
         output the calculated quantitative flow rate to the display unit, and
      c) when the number of inputs provided by the user exceeds the preset drip number, the control unit is further configured to:
         select the last inputs provided by the user up to the preset drip number,
         calculate an elapsed time that it takes for the selected inputs to be provided,
         calculate the number of drips per hour using the preset drip number and the calculated elapsed time,
         calculate the quantitative flow rate of Ringer's solution by multiplying a preset volume of each drip and the calculated number of drips per hour, and
         output the calculated quantitative flow rate to the display unit.

2. The portable device as claimed in claim 1, wherein the key input unit further includes a selection key for selecting a volume of each drip, and
   wherein the control unit is configured to store the selected volumes of each drip as the preset volume of each drop.

3. A method for measuring a flow rate of Ringer's solution using a control unit device for measuring a flow rate of Ringer's solution, the method comprising the steps of:
   (P10) receiving input from a user whenever a drip drips in a drip chamber;
   (P20) determining when the inputs provided by the user reaches a preset drip number and storing a time intervals that elapses between the inputs;
   (P30) calculating an elapsed time when the inputs provided by the user reaches the preset drip number;
   (P40) calculating the number of drips per hour using the preset drip number and the elapsed time;
   (P50) calculating a flow rate of Ringer's solution per hour by multiplying a preset volume of each drip and the number of drips per hour using the control unit device, and outputting the calculated flow rate of Ringer's solution;
   (P60) determining whether an additional input exceeding the preset drip number is provided by the user; and
   (P62) returning to step P30 and selecting the last inputs provided by the user up to the preset drip number as the inputs of the step P30 when it is determined that there is an additional input exceeding the preset drip number.

* * * * *